United States Patent [19]

DeCamp et al.

[11] Patent Number: 4,845,237

[45] Date of Patent: Jul. 4, 1989

[54] ACYLATION PROCESS FOR THE SYNTHESIS OF HMG-COA REDUCTASE INHIBITORS

[75] Inventors: Ann E. DeCamp, New Providence, now by change of name from Ann D. Schuda; Leonard M. Weinstock, Belle Mead; Thomas R. Verhoeven, Cranford, all of N.J.

[73] Assignee: Merck & Co., Inc., Rahway, N.J.

[21] Appl. No.: 38,580

[22] Filed: Apr. 15, 1987

[51] Int. Cl.$^4$ ............................................. C07F 7/18
[52] U.S. Cl. ................................... 549/214; 544/58.4; 544/69; 544/149; 544/229; 544/374; 546/14; 546/206; 546/207; 548/406; 548/517; 549/292
[58] Field of Search .................. 549/214, 292; 544/69, 544/58.4, 149, 229, 374; 546/14, 206, 207; 548/406, 517

[56] References Cited

U.S. PATENT DOCUMENTS 4,661,483 4/1987 Hoffman et al. .................... 514/236

OTHER PUBLICATIONS

H. M. R. Hoffmann, K. Haase, Synthesis, 715 (1981).
Chemical Abstracts, 72, 42844, 42845W (1970).
S. D. Saraf and M. Zaki, Synthesis, 612 (1973).

*Primary Examiner*—Richard L. Raymond
*Attorney, Agent, or Firm*—Melvin Winokur; Joseph F. DiPrima

[57] ABSTRACT

A novel acylation process using an alkali metal bromide and a dialkylaminopyridine to form a sterically hindered ester functionality from an alkanoyl chloride and an alcohol is disclosed.

18 Claims, No Drawings

ACYLATION PROCESS FOR THE SYNTHESIS OF HMG-COA REDUCTASE INHIBITORS

BACKGROUND OF THE INVENTION

Semi-synthetic and totally synthetic analogs of the natural fermentation products compactin and mevinolin have been found to be useful in limiting cholesterol biosynthesis by inhibiting the enzyme HMG-CoA reductase. Most semi-and totally synthetic analogs have the following general structural formulae:

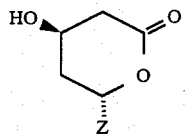

or the dihydroxy acid, salt or ester thereof, wherein Z is

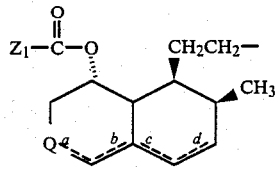

wherein Q is

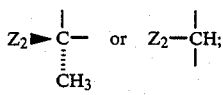

$Z_2$ is H or OH;

$Z_1$ is straight chain or branched $C_{1-10}$ alkyl, or $C_{1-10}$ alkyl substituted with hydroxyl, phenyl or substituted phenyl, cycloalkyl, $C_{1-8}$ alkanoyloxy, alkylthio or phenylthio; a, b, c, and d represent optional double bonds, especially where b and d represent double bonds or a, b, c, and d are all single bonds; provided that when a is a double bond Q is

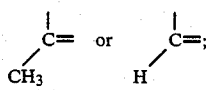

or Z is

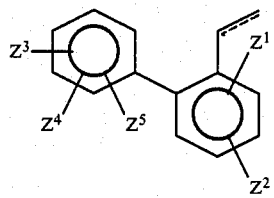

and dihydroxy acid salts and esters thereof, where $Z^1$, $Z^2$, $Z^3$, $Z^4$ and $Z^5$ independently are hydrogen,
halogen,
$C_{1-4}$alkyl,
$C_{1-4}$ haloalkyl,
hydroxy-$C_{1-4}$alkyl
$C_{1-8}$alkanoyloxy $C_{1-4}$alkyl, or
$C_7$ or $C_{11}$ aroyloxy-$C_{1-4}$alkyl
wherein one of $Z^1$, $Z^2$, $Z^3$, $Z^4$, $Z^5$ contains an ester functionality.

In the polyhydronapthyl derivatives the C-8-ester functionality is typically inserted by acylation of the C-8-alcohol with the appropriate acyl chloride. This reaction generally requires prolonged high temperatures (100° C., 18–36 hours) and large excesses of the often difficult to obtain acid chloride; however, even under these conditions the yields are low. In addition, the conditions of the acyl chloride reaction lead to a high percentage of undesired side product whereby a tertbutyldimethylsilyloxy radical, often present as a protecting group of alcohols, is eliminated from the δ-valerolactone moiety. Large amounts of starting alcohol and unconsumed acid chloride typically remain at the end of the reaction. These contaminants complicate isolation of product and result in lower yields of ester. The impurities also interfere with crystallization of subsequent intermediates. Similar problems may occur with acylation of alcohols in the biphenyl lactone derivatives, particularly where the alcohol involved is sterically hindered.

Acyl bromides are known in the literature (Chem Abstracts, 72, 42844 (1970) and S. D. Saraf, M. Zakai, Synthesis, 612 (1973)). The synthesis of acyl iodides from acyl chlorides and sodium iodide in acetonitrile has been described by Hoffman and Haase, Synthesis, 715, (1981).

DETAILED DESCRIPTION OF THE INVENTION

This invention relates to a novel acylation process for the preparation of antihypercholesterolemic compounds of structural formula (I),

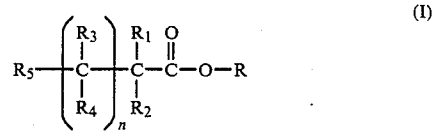

wherein:
n is 0 to 5
$R_1$ and $R_2$ are independently H or $C_{1-10}$ alkyl or $R_1$ and $R_2$ together with the carbon atom to which they are attached form a carbocyclic ring of 3 to 8 carbon atoms;
$R_3$ and $R_4$ are independently H or $C_{1-3}$ alkyl, $C_{3-7}$cycloalkyl, $C_{1-3}$alkylthio, phenyl, phenylthio or substituted phenyl in which the substituents are X and Y and when n is 2 to 5, each of the $R_3$s and $R_4$s are independently hydrogen, $C_{1-3}$ alkyl, $C_{3-7}$ cycloalkyl or only one of the $R_3$s and $R_4$s is phenyl or substituted phenyl;
$R_5$ is hydrogen, halogen, $C_{1-10}$alkyl, phenyl or substituted phenyl in which the substitutents are X and Y, or $R_5$ is a group selected from:
(a) trialkylsilyloxy-$C_{1-10}$ alkyl such as tert-butyldimethylsilyloxy-$C_{1-10}$alkyl or a like hydroxyl protecting group;

(b) triphenylmethylthio-$C_{1-10}$alkyl;
(c) $C_{1-8}$alkanoyloxy-$C_{1-4}$alkyl;
(d)

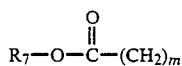

in which m is 0 to 3 and $R_7$ is $C_{1-5}$ alkyl;
(e)

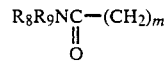

in which $R_8$ and $R_9$ are independently $C_{1-5}$ alkyl or $R_8$ and $R_9$ together with the nitrogen atom to which they are attached form a heterocycle selected from piperidinyl, morpholinyl, pyrrolidinyl, piperazinyl or thiomorpholinyl;
(f)

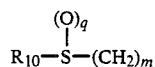

in which q is 0 to 2 and $R_{10}$ is $C_{1-5}$ alkyl or phenyl;
X and Y independently are hydrogen, halogen, trifluromethyl, $C_{1-3}$alkyl, $C_{1-3}$alkyloxy, $C_{1-3}$ alkylthio,

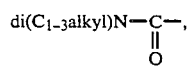

and

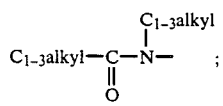

and OR is
(a)

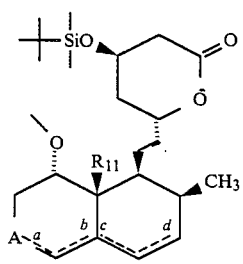

wherein
$R_{11}$ is hydrogen, or trialkylsilyloxy or alkyldiarylsilyloxy;
A is

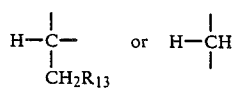

in which
$R_{13}$ is hydrogen or trialkylsilyloxy or alkyldiarylsilyloxy, a, b, c, d represent single bonds, one of a, b, c, or d represents a double bond or both a and c or both b and d represent double bonds, provided that when a is a double bond, A is

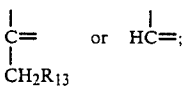

or
(b)

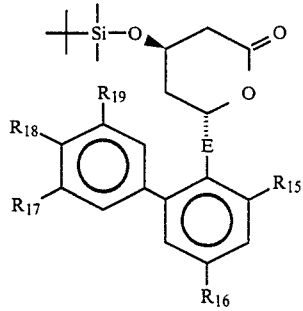

wherein
E is $CH_2$—$CH_2$ or $CH\!=\!CH$; $R_{15}$ $R_{16}$ $R_{17}$ $R_{18}$ and Rhd 19 independently are
hydrogen,
halogen,
$C_{1-4}$alkyl,
$C_{1-4}$haloalkyl,
oxy-$C_{1-4}$alkyl,
$C_{1-8}$ alkanoyloxy-$C_{1-4}$ alkyl,
$C_{8-12}$ aralkanoyloxy-$C_{1-4}$ alkyl, or $C_7$ or $C_{11}$ aroyloxy-$C_{1-4}$ alkyl, with the proviso that one of $R_{15}$ $R_{16}$ $R_{17}$ $R_{18}$ and $R_{19}$ is oxy-$C_{1-4}$alkyl or oxy- wherein oxy- the oxygen is directly bonded to an aromatic ring of the biphenyl moiety;
which comprises combining,

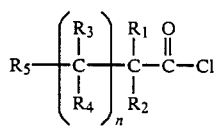

an alkali metal bromide, dialkylaminopyridine and a compound of structure (i),
(i)

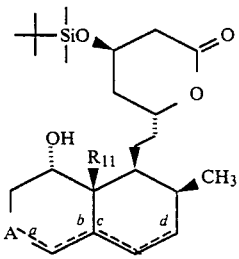

or a compound of structure (ii),
(ii)

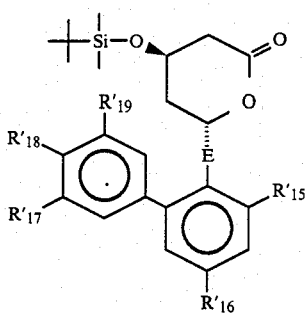

wherein
R'$_{15}$ R'$_{16}$ R'$_{17}$ R'$_{18}$ R'$_{19}$ are defined as R$_{15}$ R$_{16}$ R$_{17}$ R$_{18}$ R$_{19}$ respectively provided that when R$_{15}$ R$_{16}$ R$_{17}$ R$_{18}$ or R$_{19}$ is oxy-C$_{1-4}$alkyl or oxy- then R'$_{15}$ R'$_{16}$ R'$_{17}$ R'$_{18}$ or R'$_{19}$ is hydroxy-C$_{1-4}$ alkyl or hydroxy- respectively;
in a solvent, to yield compound (I).

The invention is an improved method for the acylation of a hindered alcohol under/or a hindered acyl chloride. The fundamental principle is the activation of an acyl chloride using an alkali metal bromide/dialkylaminopyridine in reaction with an alcohol. Although the structure of the in situ generated acylating agent (2) is unknown it may be the acyl bromide (2a) or where the solvent is pyridine a pyridinium complex (2b) or a dialkylaminopyridinium complex (2c).

The sequence below displays a typical reaction scheme:

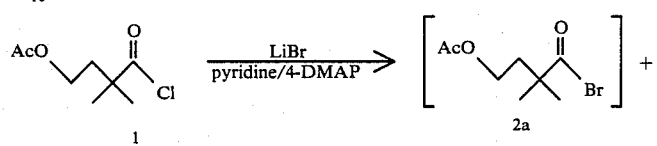

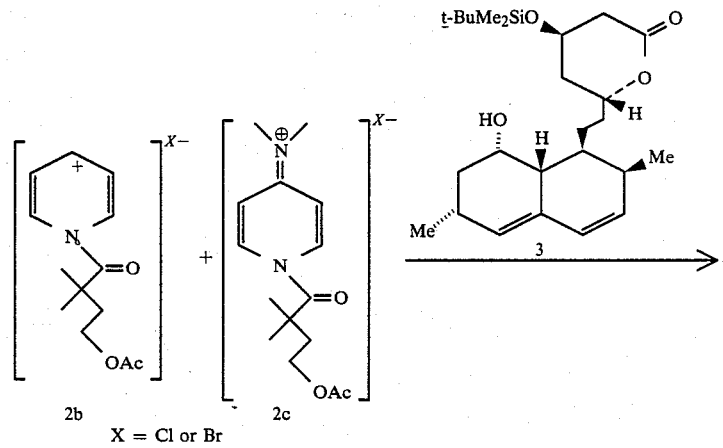

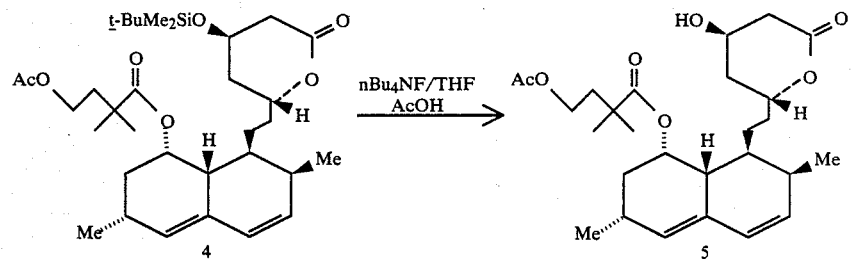

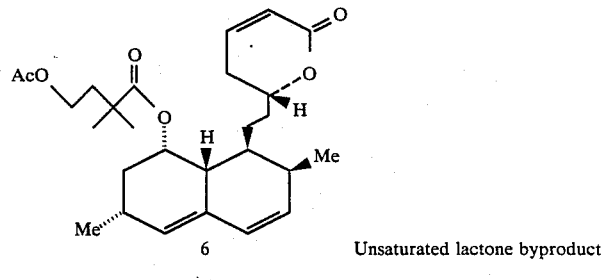

Unsaturated lactone byproduct

Following the sequence from (1) to (5) the acid chloride (1) reacts with an alkali metal bromide in a solvent followed by addition of dialkylaminopyridine. In this way the highly reactive acylating agent is available to acylate the alcohol (3) to give the ester (4) with virtually complete consumption of starting alcohol at a lower temperature (70° C.) for shorter periods of time (6–8 hours). The reaction conditions of the instant invention are compatible with the silyl-protecting groups and thus only a minimal amount (1–2%) of unsaturated by-product (6) is formed. The increased purity of the product mixture greatly simplifies the isolation procedures.

As indicated above acylation following the instant invention is advantageous compared to using the acyl chloride itself, furthermore the instant invention is also advantageous compared to using acyl bromides. The instant invention uses acid chlorides which are readily prepared and purified and can be stored indefinitely due to their relative stability towards hydrolytic decomposition. In contrast, the preparation of acid bromides requires expensive, hard to obtain reagents and distillative purification of acyl bromides is hampered by their high boiling point and instability.

The invention disclosed is applicable to all acylation reactions between an acyl chloride and an alcohol which would occur albeit in low yield without the improvement conditions of the present invention. The invention is particularly applicable to hindered alcohol and acyl chloride reactants and such reactants which demonstrate elimination under normal acylation conditions.

One embodiment of this invention is the compounds prepared by the process disclosed herein where OR is the alkoxy residue of alcohol type (i):

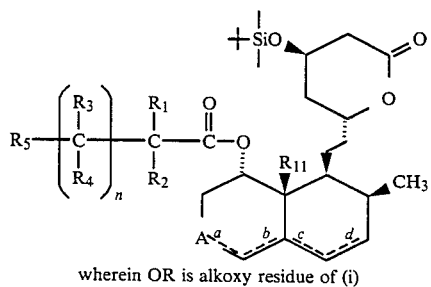

wherein OR is alkoxy residue of (i)

In one class of this embodiment the compounds prepared by the process of this invention are those compounds of formula (I) wherein $R_5$ is trialkylsilyoxy-$C_{1-3}$alkyl. In a subclass are the compounds prepared wherein $R_1$ is methyl, $R_{11}$ is hydrogen and a, b, c, d are all single bonds or one of b, c or d is a double bond or b and d are double bonds. Illustrative of this subclass are the following compounds:

(a) 6(R)-[2-[8(S)-(2,2-Dimethyl-4-tert-butyldimethylsilyloxy-butyryloxy)-2(S),6(R)-dimethyl-1,2,6,7,8,8a(R)-hexahydronaphthyl-1(S)ethyl]-4(R)-tert-butyldimethylsilyloxy-3,4,5,6-tetrahydro-2H-pyran-2-one.

(b) 6(R)-[2-[8(S)-(2,2-Dimethyl-4-tert-butyldimethylsilyloxy-pentanoyloxy)-2(S),6(R)-dimethyl-1,2,6,7,8,8a(R)-hexahydronaphthyl-1(S)ethyl]-4(R)-tert-butyldimethylsilyloxy-3,4,5,6-tetrahydro-2H-pyran-2-one.

In a second class of this embodiment are the compounds prepared wherein $R_5$ is triphenylthio-$C_{1-3}$alkyl. In a subclass are the compounds prepared wherein $R_1$ is methyl, $R_{11}$ is hydrogen and a, b, c, d are all single bonds or one of b, c, d is a double bond or b and d are double bonds. Illustrative of this subclass is the following compound:

(a) 6(R)-[2-[8(S)-(2,2-Dimethyl-4-triphenylmethylthiobutyrlyloxy)2(S),6(R)-dimethyl-1,2,6,7,8,8a(R)-hexahydronaphthyl-1(S)ethyl]-4(R)-tert-butyldimethylsilyloxy-3,4,5,6-tetrahydro-2H-pyran-2-one.

In a third class of this embodiment are the compounds prepared wherein $R_5$ is $C_{1-3}$alkanoyloxy-$C_{1-3}$alkyl. In a subclass are the compounds prepared wherein $R_1$ is methyl, $R_{11}$ is hydrogen and a, b, c, d are all single bonds or one of b, c or d is a double bond or b and d are double bonds. Illustrative of this subclass is the following compound:

(a) 6(R)-[2-[8(S)-(4-Carbomethoxy-2,2-dimethylbutyrlyloxy)-2(S),6(R)-dimethyl-1,2,6,7,8,8a(R)-hexahydronaphthyl-1(S)ethyl]4(R)-tert-butyldimethylsilyloxy-3,4,5,6-tetrahydro-2H-pyran-2-one.

A fourth class of this embodiment are the compounds prepared wherein $R_5$ is $C_{1-3}$alkyloxyacyl$(CH_2)_m$ where m is 0 to 3. In a subclass are the compounds prepared wherein $R_1$ is methyl, $R_{11}$ is hydrogen and a, b, c, d are all single bonds or one of b, c or d is a double bond or b and d are double bonds. Illustrative of this subclass are the following compounds:

(a) 6(R)-[2-[8(S)-(4-Acetyloxy-2,2-dimethylbutyrylox-y)2(S),6(R)-dimethyl-1,2,6,7,8,8a(R)-hexahydronaphthyl-1(S)ethyl]-4(R)-tert-butyldimethylsilyloxy-3,4,5,6-tetrahydro-2H-pyran-2-one.

(b) 6(R)-[2-[8(S)-(2,2-dimethylbutyryloxy)-6(R)-tert-butyldimethylsilylmethyl-2(S)-methyl-1,2,4a(R)5,6,7,8-,8a(R)-octahydro-naphthyl-1(S)ethyl]-4(R)-tert-butyldimethylsilyloxy-3,4,5,6-tetrahydro-2H-pyran-2-one.

A fifth class of this embodiment are the compounds prepared wherein $R_5$ is di

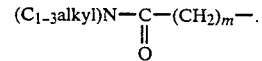

In a subclass are the compounds prepared wherein $R_1$ is methyl, $R_{11}$ is hydrogen and a, b, c, d are all single bonds or one of b, c or d is a double bond or b and d are double bonds. Illustrative of this subclass is the following compound:

(a) 6(R)-[2-[8(S)-(2,2-Dimethyl-4-(N-methylacetamido)-butyrlyloxy)-2(S),6(R)-dimethyl-1,2,6,7,8,8a(R)-hexahydronaphthyl-1(S)ethyl]-4(R)-tert-butyldimethylsilyloxy-3,4,5,6-tetrahydro-2H-pyran-2-one.

A sixth class of this embodiment are the compounds prepared wherein $R_5$ is $C_{1-3}$ alkylthio-$(CH_2)_m$, phenylthio-$(CH_2)_m$, or $C_{1-3}$ alkylsulfinyl-$(CH_2)_m$ or phenylsulfinyl-$(CH_2)_m$. In a subclass are the compounds prepared wherein $R_1$ is methyl, $R_{11}$ is hydrogen and a, b, c, d are all single bonds or one of b, c or d is a double bond or b and d are double bonds. Illustrative of this subclass is the following compound:

(a) 6(R)-[2-[8(S)-(2,2-Dimethyl-4-thiomethylbutyrylox-y)-2(S),6(R)-dimethyl-1,2,6,7,8,8a(R)-hexahydronaphthyl-1(S)ethyl]-4(R)-tert-butyldimethylsilyloxy-3,4,5,6-tetrahydro-2H-pyran-2-one.

In a seventh class of this embodiment are the compounds prepared wherein $R_5$ is phenyl or phenyl substituted with X and Y. In a subclass are the compounds prepared wherein $R_1$ is methyl, $R_{11}$ is hydrogen, and a, b, c, d are all single bonds or one of b, c or d is a double bond or b and d are double bonds. Illustrative of this subclass is the following compound:

(a) 6(R)-[2-[8(S)-(2,2-Dimethyl-4-phenylbutyryloxy)-2(S),6(R)-dimethyl-1,2,6,7,8,8a(R)-hexahydronaphthyl- 1(S)ethyl]-4(R)-tert-butyldimethylsilyloxy-3,4,5,6-tetrahydro-2H-pyran-2-one.

An eighth class of this embodiment are the compounds prepared wherein $R_5$ is $C_{1-3}$alkyl. In a subclass are the compounds prepared wherein $R_1$ is methyl, $R_{11}$ is hydrogen, and a, b, c, d are all single bonds or one of b, c or d is a double bond or b and d are double bonds. Illustrative of this subclass is the following compound:
(a) 6(R)-[2-[8(S)-(2,2-Dimethylhexanoyloxy)-2(S),6(R)-dimethyl-1,2,6,7,8,8a(R)-hexahydronaphthyl1(S)ethyl]-4(R)-tert-butyldimethylsilyloxy-3,4,5,6-tetrahydro-2H-pyran-2-one.

Another embodiment of this invention is the compounds of formula (I) prepared by the process disclosed herein where OR is the alkoxy residue of alcohol type (ii).

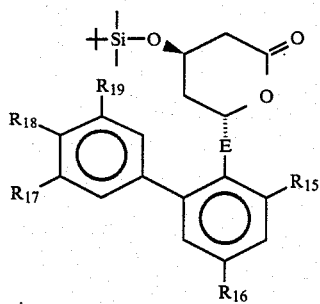

Alcohol (ii)

In one class of this embodiment are the compounds prepared wherein alcohol type (ii) E is $CH_2CH_2$ or $CH=CH$ and $R_{15}$ $R_{16}$ $R_{17}$ $R_{18}$ and $R_{19}$ independently are hydrogen, fluoro, $C_{1-4}$alkyl or hydroxy-$C_{1-4}$alkyl. In a subclass the compounds prepared by the process of this invention are those of formula (I) wherein alcohol type (ii) E is $CH=CH$. Illustrative of this subclass is the following compound:
(a) (4R,6S)-E-6-[2-(3,5-Dimethyl-4'-fluoro-3'-hydroxymethyl[1,1'-biphenyl]-2yl)ethenyl]-3,4,5,6-tetrahydro-4-hydroxy-2H-pyran-2-one.

In a second subclass are those compounds of formula (I) wherein alcohol type (ii) E is $CH_2CH_2$. Illustrative of this subclass is the followiing compound:
(a) (4R,6S)-6-[2-(3,5-Dimethyl-4'-fluoro-3'-hydroxymethyl[1,1'-biphenyl]-2-yl)ethyl]-3,4,5,6-tetrahydro-4-hydroxy-2H-pyran-2-one.

In the instant invention the acyl chloride, alcohol, alkali metal bromide and dialkylaminopyridine catalyst may be combined in any sequence. Preferably the acyl chloride is combined with an anhydrous alkali metal bromide in the appropriate solvent under an inert atmosphere for approximately 10-15 minutes before combination with the alcohol. Illustrative of appropriate solvents are: pyridine, 1,2 dichloroethane, methylene chloride, triethylamine and mixtures of pyridine with tetrahydrofuran, diethyl ether and methylene chloride.

The preferred solvent is pyridine. The preferred alkali metal bromide is lithium bromide.

The mole ratio of alkali metal bromide to acyl chloride can vary between 1.0-10.0 mole equivalents alkali metal bromide to 1.0 mole equivalent acyl chloride. The preferred rato is 2.0 mole equivalents metal bromide to 1 equivalent acyl chloride. It is critical that the alkali metal bromide be dried prior to use and that it not thereafter be exposed to the atmosphere.

The mole ratio of acyl chloride to alcohol can vary between 2.0 to 3.0 mole equivalents of acyl chloride to 1.0 mole equivalents of alcohol. The preferred ratio is 2 equivalents acyl chloride to 1 equivalent alcohol. The acyl chloride is treated with an alcohol and an appropriate catalyst.

The catalysts employed are N, N, dialkylaminopyridines and cycloalkylated aminopyridines including 4-N,N-dimethylaminopyridine, 4-pyrollidnopyridine, 4-(2,5-dimethyl)pyrollidinopyridine and N,N,N',N'-tetramethyl-N''-4-pyridinyl-guanidine. The preferred catalyst is 4-N,N-dimethylaminopyridine. The amount of catalyst employed is approximately 0.1 mole equivalent to 1.0 mole equivalent acyl chloride.

The mixture of reactants, solvent and catalyst is heated between 25°–75° C., preferably 70°–75° C. for 6–8 hours.

General reaction sequence:

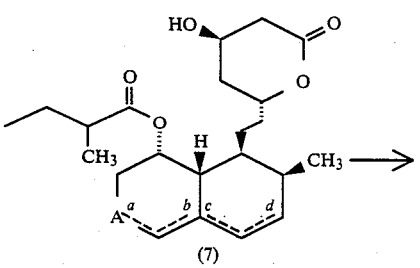

(7)

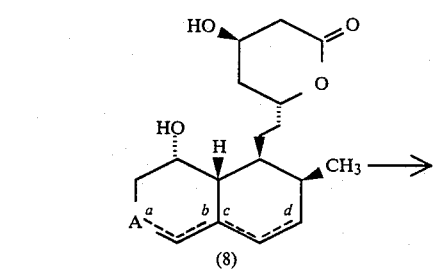

(8)

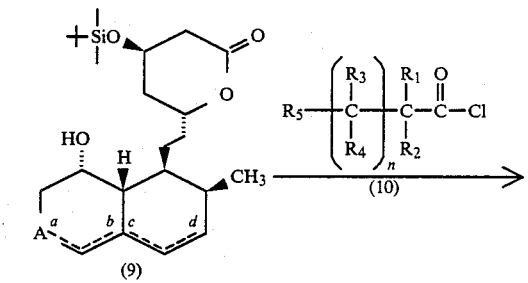

(9)

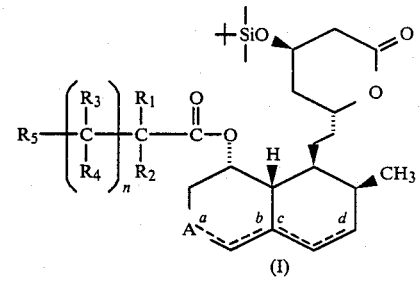

(I)

In using the process wherein the reactant alcohol is of type (i) the precusor starting materials are compactin, mevinolin and their dihydro and tetrahydro analogs which are readily available or may be prepared according to fermentation procedures disclosed in U.S. Pat. No. 3,983,140, U.S. Pat. No. 4,049,495, U.S. Pat. No. 4,231,938, U.S. Pat. No. 4,294,846 and U.S. Pat. No. 4,343,814, and the hydrogenation procedures disclosed in U.S. Pat. No. 4,351,844. Reactants which contain a hydroxymethyl or a protected hydroxymethyl group in the 6-position of the polyhydronaphthyl ring are prepared according to the procedures disclosed in copending U.S. application Ser. No. 001,933 filed Jan. 9, 1987, now abandoned. The appropriate starting material of formula (7) is then hydrolyzed under the conditions disclosed in U.S. Pat. No. 4,444,784 to afford the compounds of formula (8). The 4-hydroxy function in the lactone moiety of the compounds of formula (8) is protected with a suitable protecting agent, exemplified here as a dimethyl-t-butylsilyl group according to the procedure disclosed in U.S. Pat. No. 4,444,784. Acylation of the 8'-hydroxy group is then accomplished using the appropriate acyl chloride, an alkali metal bromide and a dialkylaminopyridine catalyst. Silyl protecting groups are removed by treatment with tetra-butyl-ammonium fluoride following the procedure detailed in U.S. Pat. No. 4,444,784. Triphenylmethyl protecting groups are removed by treatment with dilute acid.

The appropriately substituted acyl chlorides of formula (10) are commercially available or prepared from known starting materials utilizing standard chemical transformations. Specific examples of such transformations can be found in the following references:

| where $R_5$ is | Reference |
|---|---|
|  or | copending U.S. patent application Serial No. 859,534, filed May 5, 1986, now abandoned, and incorporated herein by reference. In a typical preparation phenylacetic or an X,Y substituted phenylacetic acid is alkylated at the alpha position. The acid is then converted into the acid chloride using oxalylchloride. |
| $R_7-O-\overset{O}{\underset{\|}{C}}-(CH_2)_m$ | copending U.S. patent applications Serial No. 859,535, filed May 5, 1986, now U.S. Pat. No. 4,771,071, Serial No. 859,525, filed May 5, 1986, now U.S. Pat. No. 4,766,145, and incorporated herein by reference. The appropriately substituted diester is converted to the monoester acid which is treated with oxalylchloride to form the desired ester substituted acyl chloride. |
| $R_8R_9N\overset{O}{\underset{\|}{C}}-(CH_2)_m$ | copending patent application Serial No. 859,529, filed May 5, 1986, now U.S. Pat. No. 4,661,483, and incorporated herein by reference. An ester substituted acyl chloride prepared as described above is treated with a $R_8R_9$ substituted amine to yield an amide substituted ester which is further converted to the amide substituted acid and finally upon treatment with oxalyl chloride to the desired amide substituted acyl halide. |

-continued

| where $R_5$ is | Reference |
|---|---|
| $R_{10}-\overset{(O)_q}{\underset{\|}{S}}-(CH_2)_m$ | copending patent applications Serial No. 859,530, filed May 5, 1986, now abandoned, 859,513, filed May 5, 1986, now abandoned, and incorporated herein by reference. In a typical preparation a bromo ester is treated with an appropriate alkyl or aryl mercaptan to form a thio substituted ester which is converted to the thio substituted acid and upon treatment with oxalyl chloride to the desired thio substituted acyl chloride. Conversion to the sulfinyl or sulfonyl derivatives can be accomplished upon oxidation with 3-chloroperoxybenzoic acid. |

Reactant alcohols of type (ii) are prepared from starting materials utilizing standard chemical transformations specific examples of such procedures are found in copending patent application Ser. Nos. 902,894 filed Sept. 2, 1986 and 824,900 filed Jan. 31, 1986, now U.S. Pat. No. 4,772,626.

The following examples illustrate the present invention and as such are not to be considered as limiting the invention set forth in the claims appended hereto.

EXAMPLE 1

Preparation of 6(R)-[2-[8(S)-(4-Acetyloxy-2,2-dimethylbutyryloxy)-2(S),6(R)-dimethyl-1,2,6,7,8,8a(R)-hexahydronaphthyl-1(S)]ethyl]-4(R)-tert-butyldimethylsilyloxy-3,4,5,6-tetrahydro-2H-pyran-2-one A dry 50 L 3-necked, round bottom flask, fitted with an overhead stirrer, thermocouple, and condenser was charged with 2,2-dimethyl-4-acetoxybutyryl chloride (1.639 kg, 8.51 moles) and 6.8 L of dry pyridine and agitated under a N₂ atmosphere. Anhydrous lithium bromide (1.46 kg, 16.98 moles) was added portionwise over a period of 15 minutes via a plastic bag secured to the neck of the flask. Commercial anhydrous lithium bromide (Aldrich, 99+%) was dried in vacuo at 135° C. for 3 days prior to use.

The internal temperature rose to 55°-60° C. during the addition of LiBr to the pyridine/acid chloride mixture and the color changed from yellowish red to reddish brown.

The mixture was allowed to stir for 10-15 minutes at ambient temperature. A solution of 6R-[2-8(S)-hydroxy-2(S),6(R)-dimethyl-1,2,6,7,8,8a(R)-hexahydronaphthyl-1(S)-ethyl]-4(R)-tert-butyldimethylsilyloxy-3,4,5,6-tetrahydro-2H-pyran-2-one (1.856 kg, 4.76 moles) in 5.4 L of dry pyridine was added in one portion. 4-N,N-Dimethylaminopyridine (104 g, 0.85 mole) was added and the mixture heated at 75° C. under N₂. The reaction mixture turned dark brown as it was heated. The progress of the reaction was monitored by hplc. The reaction was typically carried to 98-99% conversion (usually 6-8 hours at 75° C.). Product area % was usually 91-94%. At this point the level of unsaturated lactone by-product was approximately 1.5-1.8%. Prolonged heating increased the level of this impurity.

The reaction mixture was cooled to room temperature and some of the pyridine (6 L) removed in vacuo.

The thick, brown mixture was diluted with 4 L of ethyl acetate and 2 kg of ice and cooled to 15° C. as the pH was adjusted to 2.7 with 6N HCl (7700 mL).

The acid was added at such a rate to keep the temperature <20° C. The pH was monitored with a pH meter.

More ethyl acetate (8 L) was added with vigorous agitation and the phases separated. The aqueous phase was further extracted with 12 L and 8 L portions of ethyl acetate. The combined organic phases were washed with 6 L of 1.2N HCl solution, 2×8 L of saturated NaHCO3 solution and 8 L of saturated brine, dried over Na2SO4 (under N2), filtered and evaporated in vacuo to a viscous, dark brown oil, which is used directly in the next step. The title compound was purified by column chromatography on silica gel using 25% ethyl acetate in hexanes to elute. The pure product was isolated as a colorless oil $^1$H NMR (250 MHz, CDCl3) 5.90 (d, 1H, J=10.0 Hz), 5.77 (dd, 1H, J=10.0, 6.3 Hz), 5.50 (t, 1H, J=3.75 Hz), 5.28–5.44 (m, 1H), 4.44–4.71 (m, 1H), 4.22–4.36 (m, 1H), 3.93–4.19 (m, 2H), 0.40–2.75 (m, 24H; containing 3H singlet at 2.01, 3H singlet at 1.19, 3H singlet at 1.18, 3H doublet (J=7.5 Hz) at 1.07, 12H singlet at 0.87 (tert-butyl and methyl), 0.70 (s, 3H), 0.65 (s, 3H). IR(neat) 3020, 2960, 2940, 1738, 1475, 1370, 1240 cm$^{-1}$.

EXAMPLE 2

Preparation of 6(R)-[2[8(S)-(2,2-dimethylbutyryloxy)-2(S),6(R)-dimethyl-1,2,6,7,8,8a(R)-hexahydronaphthyl-1(S)]ethyl]-4(R)-tert-butyldimethylsilyloxy-3,4,5,6-tetrahydro-2H-pyran-2-one Lithium bromide (2.95 g, 34 mmol, anhydrous) was added as rapidly as possible to a solution of 2,2-dimethylbutyryl chloride (2.28 g, 17 mmol) in anhydrous pyridine (13 mL) under N2. When the temperature returned to 25° C., a solution of the alcohol (3.71 g, 8.51 mmol) and 4,4-dimethylaminopyridine (0.208 g, 1.7 mmol) in pyridine (10 mL) was added. The mixture was stirred at 70° C. for 3.5 hours. The mixture was cooled to room temperature, poured into H2O (100 mL) and extracted with 2×100 mL of ethyl acetate. The combined organic extracts were washed with 2×50 mL of 1.2N HCl, 50 mL of saturated NaHCO3 solution, 50 mL of saturated brine, dried over anhydrous Na2SO4, filtered and evaporated in vacuo to give the title compound as a colorless oil. $^1$H NMR (300 MHz, CDCl3) 5.97 (d, 1H, J=9.75 Hz), 5.75 (dd, 1H, J=9.75, 6.15 Hz), 5.43–5.52 (m, 1H), 5.26–5.35 (m, 1H), 4.48–4.64 (m, 1H), 4.22–4.33 (m, 1H), 2.17–2.65 (m, 5H), 0.70–2.05 (m, 35H; containing two 3H singlets at 1.11 and 1.08 ppm and a 9H singlet at 0.85 ppm), 0.06 (s, 3H), 0.05 (s, 3H).

EXAMPLE 3–15

Following the procedure in Examples 1 and 2 the following compounds of Formula (I) are prepared:

| Example | OR | $R_1$ | $R_2$ | $R_3$ | $R_4$ | $R_5$ | n |
|---|---|---|---|---|---|---|---|
| 3. | 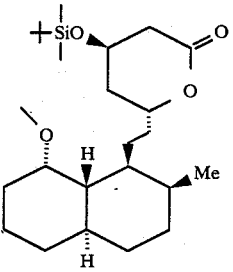 | Me | Me | H | H | Me | 1 |
| 4. | " | Me | Me | H | H | AcOCH2 | 1 |
| 5. | " | —CH2CH2CH2CH2CH2— | | H | H | Me | 1 |
| 6. | 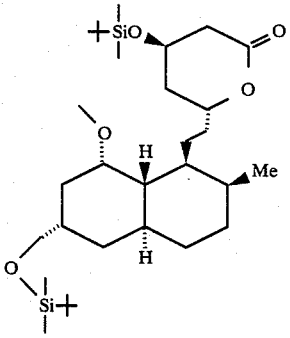 | Me | Me | H | H | Me | 1 |
| 7. | " | Me | Me | H | H | AcOCH2 | 1 |
| 8. | " | —CH2CH2CH2CH2CH2— | | H | H | Me | 1 |

-continued
| Example | OR | R₁ | R₂ | R₃ | R₄ | R₅ | n |
|---|---|---|---|---|---|---|---|
| 9. | 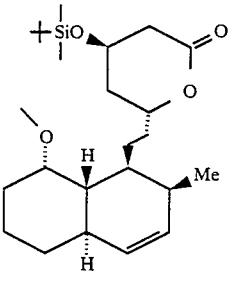 | Me | Me | H | H | Me | 1 |
| 10. | " | Me | Me | H | H | AcOCH₂ | 1 |
| 11. | " | —CH₂CH₂CH₂CH₂CH₂— | | H | H | Me | 1 |
| 12. | 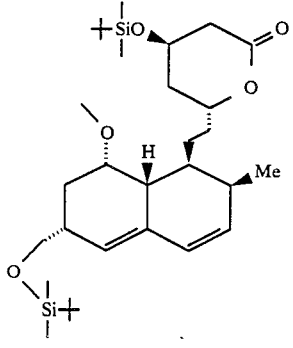 | Me | Me | H | H | Me | 1 |
| 13. | " | Me | Me | H | H | AcOCH₂ | 1 |
| 14. | " | —CH₂CH₂CH₂CH₂CH₂— | | H | H | Me | 1 |
| 15. | 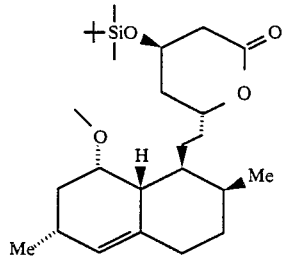 | Me | Me | H | H | Me | 1 |
| 16. | 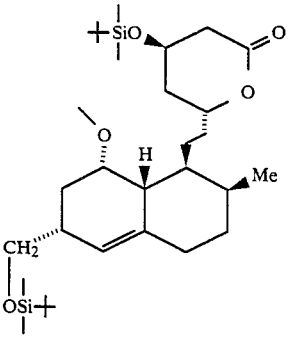 | Me | Me | H | H | Me | 1 |
What is claimed is:
1. A process for the preparation of compounds of structural formula (I),

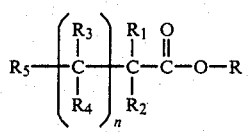 (I)

wherein:
n is 0 to 5
$R_1$ and $R_2$ are independently H or $C_{1-10}$ alkyl or $R_1$ and $R_2$ together with the carbon atom to which they are attached form a carbocyclic ring of 3 to 8 carbon atoms;
$R_3$ and $R_4$ are independently H or $C_{1-3}$ alkyl, $C_{3-7}$ cycloalkyl, $C_{1-3}$ alkylthio, phenyl, phenylthio or substituted phenyl in which the substituents are X and Y and when n is 2 to 5, each of the $R_3$s and $R_4$s are independently hydrogen, $C_{1-3}$ alkyl, $C_{3-7}$ cycloalkyl or only one of the $R_3$s and $R_4$s is phenyl or substituted phenyl;
$R_5$ is hydrogen, halogen, $C_{1-10}$ alkyl, phenyl or substituted phenyl in which the substituents are X and Y, or a group selected from:
(a) trialkylsilyloxy-$C_{1-10}$alkyl or alkyldiarylsilyloxy-$C_{1-10}$alkyl;
(b) triphenylmethylthio-$C_{1-10}$alkyl;
(c) $C_{1-8}$alkanoyl-$C_{1-4}$alkyl;
(d)

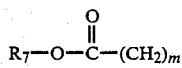

in which m is 0 to 3 and $R_7$ is $C_{1-5}$ alkyl;
(e)

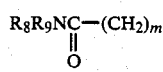

in which $R_8$ and $R_9$ are independently $C_{1-5}$ alkyl or $R_8$ and $R_9$ together with the nitrogen atom to which they are attached from a heterocycle selected from piperidinyl, morpholinyl, pyrrolidinyl, piperazinyl or thiomorpholinyl;
(f)

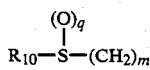

in which q is 0 to 2 and $R_{10}$ is $C_{1-5}$ alkyl or phenyl;
X and Y independently are hydrogen, halogen, trifluromethyl, $C_{1-3}$alkyl, $C_{1-3}$alkyl-oxy, $C_{1-3}$alkyl-thio,

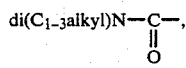

and

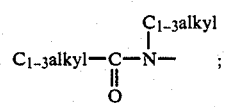

and OR is (a)

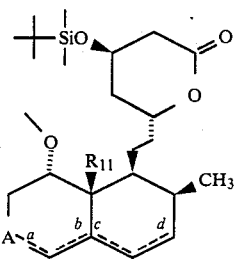

wherein
$R_{11}$ is hydrogen or trialkylsilyloxy or alkyldiarylsilyloxy;
A is

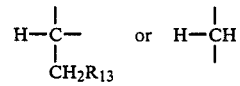

in which
$R_{13}$ is hydrogen or trialkylsilyloxy or alkyldiarylsilyloxy; a, b, c, d represent single bonds, one of a, b, c, or d represents a double bond or both a and c or both b and d represent double bonds, provided that when a is a double bond, A is

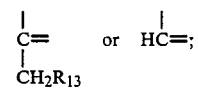

or (b)

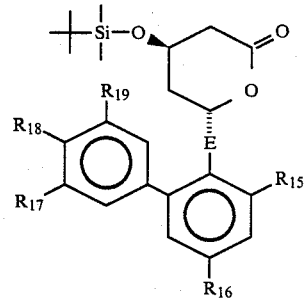

wherein
E is $CH_2$—$CH_2$ or CH=CH;
$R_{15}$ $R_{16}$ $R_{17}$ $R_{18}$ and $R_{19}$ independently are
hydrogen,
halogen,
$C_{1-4}$alkyl,
$C_{1-4}$ haloalkyl,
oxy-$C_{1-4}$ alkyl,
$C_{1-8}$ alkanoyloxy-$C_{1-4}$ alkyl,
$C_{8-12}$ aralkanoyloxy-$C_{1-4}$ alkyl, or
$C_7$ or $C_{11}$ aroyloxy-$C_{1-4}$ alkyl, with the proviso that one of $R_{15}$ $R_{16}$ $R_{17}$ $R_{18}$ and $R_{19}$ is oxy-$C_{1-4}$ alkyl or oxy- wherein oxy- the oxygen is directly bonded to the aromatic ring;
which comprises combining,

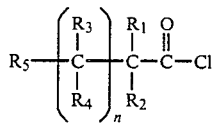

an alkali metal bromide, dialkylaminopyridine and a compound of structure (I), (i)

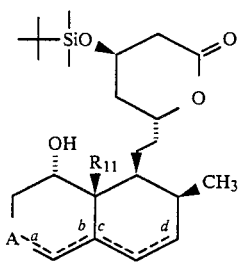

or a compound of structure (ii), (ii)

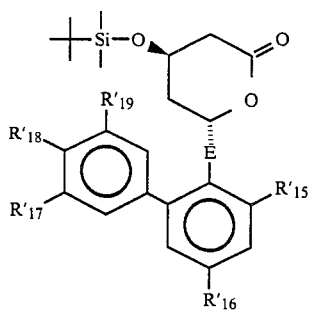

wherein
$R'_{15}$ $R'_{16}$ $R'_{17}$ $R'_{18}$ $R'_{19}$ are defined as $R_{15}$ $R_{16}$ $R_{17}$ $R_{18}$ $R_{19}$ respectively provided that when $R_{15}$ $R_{16}$ $R_{17}$ $R_{18}$ or $R_{19}$ is oxy-$C_{1-4}$alkyl or oxy- then $R'_{15}$ $R'_{16}$ $R'_{17}$ $R'_{18}$ or $R'_{19}$ is hydroxy-$C_{1-4}$-alkyl or hydroxy respectively;

in a solvent, to yield compound (I).

2. A process of claim 1 wherein OR is (a).

3. A process of claim 2 wherein $R_5$ is selected from a group consisting of:
trialkylsilyloxy-$C_{1-3}$ alkyl,
triphenylmethylthio-$C_{1-3}$ alkyl,
$C_{1-3}$alkanoyloxy-$C_{1-3}$ alkyl,

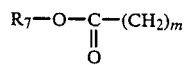

in which m is 0 to 3 and $R_7$ is $C_{1-3}$alkyl,

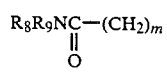

in which $R_8$, $R_9$ independently are $C_{1-3}$ alkyl,

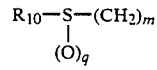

in which q is 0 to 2 and $R_{10}$ is $C_{1-3}$ alkyl, phenyl, or phenyl substituted with X and Y,
Phenyl substituted with X and Y, or $C_{1-3}$ alkyl.

4. A process of claim 3 wherein $R_1$ is methyl, $R_{11}$ is hydrogen and a, b, c, d, are all single bonds or one of a, b, c, d is a double bond or b and d are double bonds.

5. A process of claim 4 wherein $R_2$ is methyl, $R_3$ and $R_4$ are hydrogen.

6. A process of claim 5 wherein $R_{13}$ is hydrogen.

7. A process of claim 2 wherein $R_5$ is $C_{1-3}$alkanoyloxy-$C_{1-3}$ alkyl.

8. A process of claim 7 wherein the compound prepared is 6(R)-[2-[8(S)-(4-Acetyloxy-2,2-dimethylbutyryloxy)-2(S)-6(R)-dimethyl-1,2,6,7,8,8a(R)-hexahydronaphthyl-1(S)]ethyl]-4(R)-tert-butyldimethylsilyloxy-3,4,5,6-tetrahydro-2H-pyran-2-one.

9. A process of claim 1 wherein OR is (b).

10. A process of claim 9 wherein E is $CH_2CH_2$ or CH=CH; $R_{15}$ $R_{16}$ $R_{17}$ $R_{18}$ $R_{19}$ independently are $C_{1-4}$ alkyl, oxy-$C_{1-4}$alkyl, hydrogen and fluoro.

11. A process of claim 10 wherein E is CH=CH; $R_{15}$ $R_{16}$ $R_{17}$ $R_{18}$ $R_{19}$ independently are methyl, oxy-methyl, fluoro, and hydrogen.

12. A process according to claim 1 wherein the alkali metal bromide is lithium bromide.

13. A process according to claim 1 wherein the solvent is selected from the group consisting of pyridine, 1,2 dichloroethane, methylene chloride, triethylamine and mixtures of pyridine with tetrahydrofuran, diethyl ether and methylene chloride.

14. A process according to claim 13 wherein the solvent is pyridine.

15. A process according to claim 1 wherein the dialkylaminopyridine catalyst is selected from a group consisting of di($C_{1-5}$alkyl)aminopyridine, 4-pyrrolidinopyridine, 4(2,5-dimethylpyrrolidino pyridine and N,N,N',N'-tetramethyl-N''-4 pyridinyl-guanidine.

16. A process according to claim 15 wherein the dialkylamino pyridine catalyst is 4,4-dimethylaminopyridine.

17. A process of claim 2 further comprising the treatment of compound (I) with tetrabutylammonium fluoride and dilute acid to form:

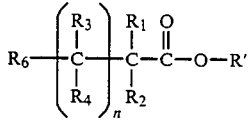

wherein
$R_6$ is defined as $R_5$ provided that trialkylsilyloxy-$C_{1-10}$ alkyl or alkyldiarylsilyloxy-$C_{1-10}$alkyl is hydroxy-$C_{1-10}$ alkyl, and triphenylmethylthio-$C_{1-10}$alkyl is thio-$C_{1-10}$alkyl;
and OR' is

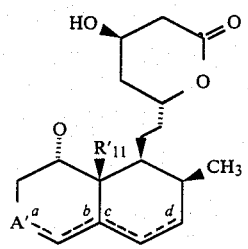

wherein

R′$_{11}$ is hydrogen or hydroxy;

A′ is

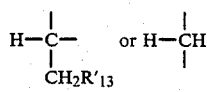

in which

R′$_{13}$ is hydrogen or hydroxy;

provided that when a is a double bond,

A′ is (a) 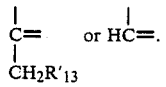

18. A process of claim 9 further comprising, the treatment of compound (I) with tetrabutyl-ammonium fluoride and dilute acid to form,

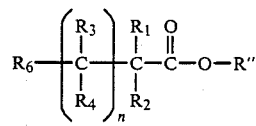

wherein

R′$_6$ is defined as R$_5$ provided that trialkylsilyloxy-C$_{1-10}$ alkyl or alkyldiarylsilyloxy-C$_{1-10}$-alkyl is hydroxy-C$_{1-10}$ alkyl and triphenylmethylthio-C$_{1-10}$ alkyl is thio-C$_{1-10}$ alkyl, and OR″ is

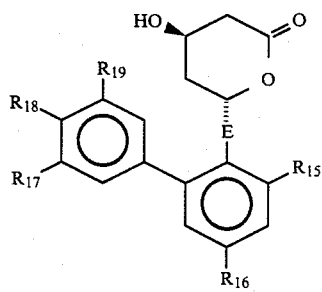

\* \* \* \* \*